(12) United States Patent
Hilpert

(10) Patent No.: US 11,312,920 B2
(45) Date of Patent: Apr. 26, 2022

(54) BOTANICAL OIL EXTRACTION METHOD AND SYSTEM

(71) Applicant: Engenuity Inc., Conroe, TX (US)

(72) Inventor: Lee Hilpert, Hollister, CA (US)

(73) Assignee: Dynamistic Technologies, LLC, Conroe, TX (US)

( * ) Notice: Subject to any disclaimer, the term of this patent is extended or adjusted under 35 U.S.C. 154(b) by 0 days.

(21) Appl. No.: 16/780,528

(22) Filed: Feb. 3, 2020

(65) Prior Publication Data

US 2020/0248098 A1     Aug. 6, 2020

Related U.S. Application Data

(60) Provisional application No. 62/802,240, filed on Feb. 7, 2019, provisional application No. 62/801,671, filed on Feb. 6, 2019, provisional application No. 62/801,672, filed on Feb. 6, 2019.

(51) Int. Cl.
| | |
|---|---|
| *C11B 1/10* | (2006.01) |
| *B01D 11/02* | (2006.01) |
| *B01D 1/06* | (2006.01) |
| *B01D 21/26* | (2006.01) |
| *C07C 51/48* | (2006.01) |

(52) U.S. Cl.
CPC ............. *C11B 1/10* (2013.01); *B01D 1/065* (2013.01); *B01D 11/0223* (2013.01); *B01D 11/0288* (2013.01); *B01D 11/0296* (2013.01); *B01D 21/26* (2013.01); *C07C 51/48* (2013.01)

(58) Field of Classification Search
CPC ....... C11B 1/10; C07C 51/48; B01D 11/0223; B01D 11/0288; B01D 11/0295; B01D 1/065; B01D 21/26
See application file for complete search history.

(56) References Cited

U.S. PATENT DOCUMENTS

| | | | | |
|---|---|---|---|---|
| 2,467,404 | A * | 4/1949 | Pascal ..................... | C11B 1/102 554/10 |
| 2,616,908 | A * | 11/1952 | Colbeth ................... | C11B 1/10 554/11 |
| 2,752,377 | A * | 6/1956 | McDonald ................ | C11B 1/10 554/21 |
| 4,944,954 | A * | 7/1990 | Strop ....................... | C11B 1/00 426/417 |
| 2016/0030860 | A1 * | 2/2016 | McGhee ................. | C11B 9/025 422/116 |

* cited by examiner

*Primary Examiner* — Yate' K Cutliff
(74) *Attorney, Agent, or Firm* — Tumey L.L.P.

(57) ABSTRACT

A method and apparatus for extracting botanical oil from botanical mass includes milling the biomass and chilling the milled biomass. The biomass is then exposed to a chilled ethanol solvent. Water is added and the solution introduced into a first centrifuge. The clean ethanol slurry is then introduced into an evaporator leaving a two-phase mixture which is introduced into a second centrifuge which separates the water from the pure botanical oil.

6 Claims, 1 Drawing Sheet

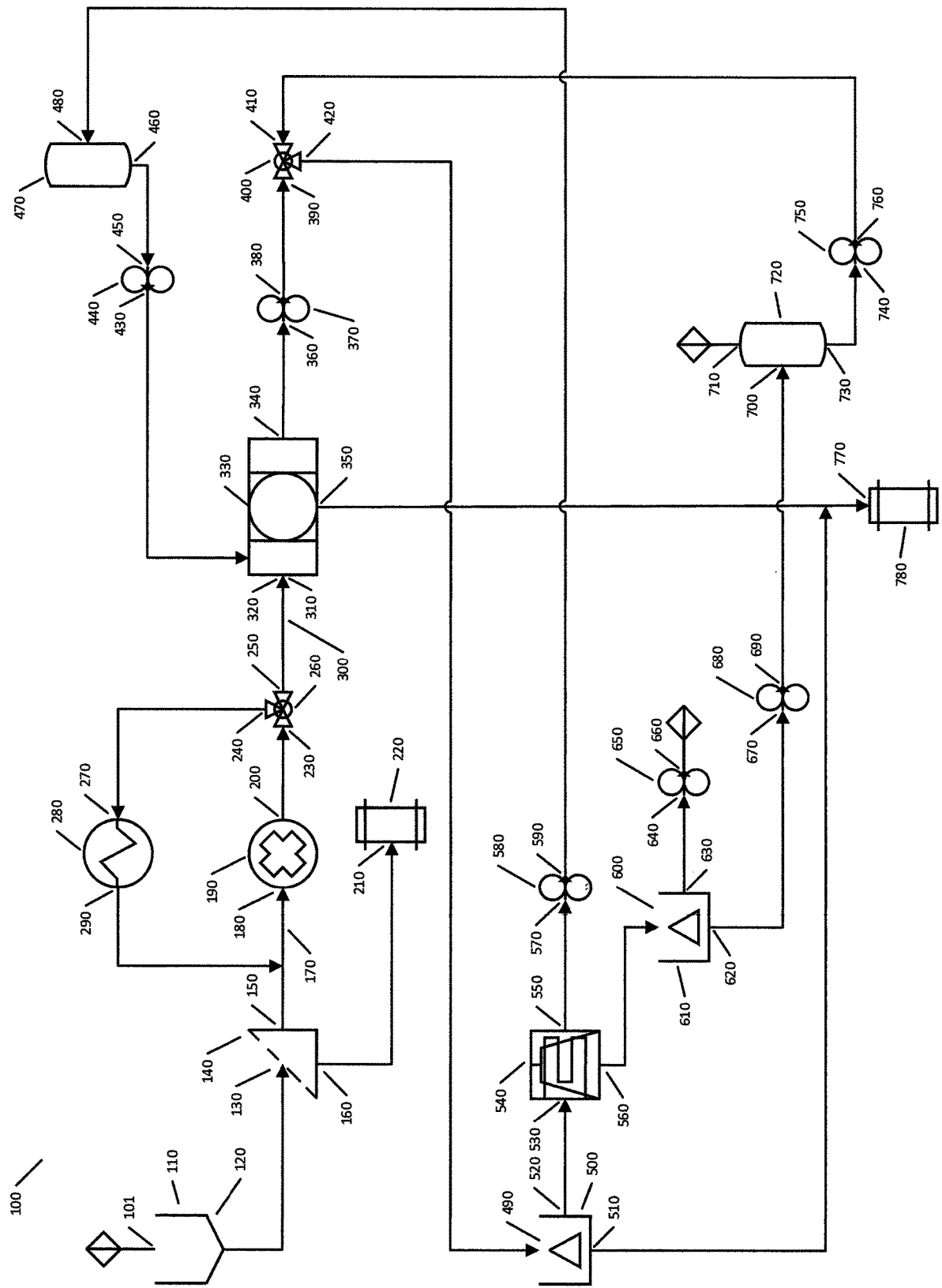

BOTANICAL OIL EXTRACTION METHOD AND SYSTEM

This non-provisional patent application claims priority to provisional application 62/802,240 filed Feb. 7, 2019, 62/801,671 filed Feb. 6, 2019, and 62/801,672 filed Feb. 6, 2019. The entire contents of each noted application are hereby incorporated by reference thereto.

BACKGROUND OF THE INVENTION

Field of the Invention

This invention is directed to a method and system for extracting botanical oil from botanical biomass.

Description of Related Arts

There are many well know mechanical and solvent based extractions methods to extract botanical oil from botanical biomass. For example; mechanically induced forces can be an effective mechanical extraction method at certain temperatures and pressures. Supercritical carbon dioxide can be an effective solvent extraction method when utilized at certain temperatures and pressures. Hydrocarbons such as butane and hexane can be an effective solvent extraction method when utilized at certain temperatures and pressures. Ethanol can be an effective solvent extraction method when utilized at certain temperatures and pressures. While all of these can be effective extraction methods of extracting botanical oil from botanical biomass, none of these extraction methods produce a pure botanical oil principally free of undesirable botanical biomass.

Ethanol solvent extractions processes are considered to be a very efficient means of extracting botanical oil. It is also a very scalable process and has one of the highest extraction rates per square foot of space of any extraction process currently utilized within the industry. However, the highly polar nature of ethanol results in the extraction of undesirable biomass if the extraction process variables are not sufficiently controlled. Current technology utilized within the industry does not provide for a means of precisely controlling the variables of the ethanol solvent extraction process to sufficiently prevent the extraction of undesirable biomass.

Therefore, there is a need for a safe and efficient ethanol solvent extraction process of botanical oil from botanical biomass that provides for precisely controlling the variables of the ethanol solvent extraction process to sufficiently prevent the extraction of undesirable botanical biomass.

The present invention addresses these and other needs by providing a system and method for safely, efficiently and precisely controlling the variables of the ethanol solvent extraction process.

BRIEF SUMMARY OF THE INVENTION

The botanical biomass is first subject to a milling process to effectively increase the surface area to volume ratio (SA:V) of the bulk botanical biomass. The milled botanical biomass is then exposed to a heat transfer process to remove heat from and thus reduce the temperature of the botanical biomass. The now chilled botanical biomass is introduced into the extractor where it is exposed to chilled ethanol solvent. The botanical oil and other solubles of the botanical biomass are solvated into solution with the chilled ethanol solvent and are discharged as a liquid solution from the extractor. The remaining botanical biomass is discharged separately as a solid for disposal. Water is added to the chilled ethanol solution causing the solids in solution to precipitate forming a chilled ethanol slurry. The slurry is then introduced into a centrifuge where it is exposed to an elevated centripetal force to remove principally all of the remaining undesirable botanical biomass. The clean ethanol solution is then introduced into an evaporator where the ethanol is removed from the solution as a vapor leaving a two-phase liquid mixture consisting of clean botanical oil and water. The multi-phase liquid mixture is then introduced into a second centrifuge where it is exposed to an elevated centripetal force to separate the two phases of the multi-phase liquid. The now separated water is disposed of leaving the now separated clean and pure botanical oil.

The following detailed description and drawings of the preferred embodiment of the Botanical Oil Extraction Method and System is intended as an exemplification of the principals of the invention and not intended to limit the invention to any specific embodiment.

BRIEF DESCRIPTION OF THE DRAWINGS

For a detailed description of the preferred embodiment of the invention, reference will be made to the accompanying drawing. FIG. 1 is a schematic showing of a system according to a first embodiment of the invention.

DETAILED DESCRIPTION OF AN EMBODIMENT

FIG. 1 depicts flow diagram 100 of the process of this invention. Flow diagram 100 includes feed hopper 110 including outlet 120. Outlet 120 of feed hopper 110 is mechanically coupled to and in conveyance communication with Inlet 130 of pre-screener 140. Outlet 150 of pre-screener 140 is mechanically coupled to and in conveyance communication with inlet 180 of Miller 190 via variable speed feed screw 170. Outlet 200 of Miller 190 is mechanically coupled to and in pneumatic communication with inlet 230 of diverter valve 260. Outlet 240 of diverter valve 260 is mechanically coupled to and in pneumatic communication with inlet 270 of heat exchanger 280. Outlet 290 of heat exchanger 280 is mechanically coupled to and in pneumatic communication with feed screw 170.

Outlet 250 of diverter valve 260 is mechanically coupled to and in pneumatic communication with feed screw 300. Feed screw 300 is mechanically coupled to and in conveyance communication with inlet 310 of extractor 330. Outlet 340 of extractor 330 is mechanically coupled to and in fluid communication with inlet 360 of pd (positive displacement) pump 370. Outlet 380 of pd pump 370 is mechanically coupled to and in fluid communication with inlet 390 of mixing valve 400. Outlet 420 of mixing valve 400 is mechanically coupled to and in fluid communication with inlet 490 of centrifuge 500. Outlet 520 of centrifuge 500 is mechanically coupled to and in fluid communication with inlet 530 of evaporator 540. Outlet 560 of evaporator 540 is mechanically coupled to and in fluid communication with inlet 600 of centrifuge 610. Outlet 630 of centrifuge 610 is mechanically coupled to and in fluid communication with inlet 640 of pd pump 650. Outlet 660 of pd pump is mechanically coupled to and in fluid communication with the clean botanical oil outlet.

Outlet 550 of evaporator 540 is mechanically coupled to and in fluid communication with inlet 570 of pd pump 580. Outlet 590 of pd pump 580 is mechanically coupled to and in fluid communication with inlet 480 of buffer tank 470. Outlet 460 of buffer tank 470 is mechanically coupled to and in fluid communication with inlet 450 of pd pump 440. Outlet 430 of pd pump 440 is mechanically coupled to and in fluid communication with inlet 320 of extractor 330.

Outlet 620 of centrifuge 610 is mechanically coupled to and in fluid communication with inlet 670 of pd pump 680. Outlet 690 of pd pump 680 is mechanically coupled to and in fluid communication with inlet 700 of buffer tank 720. Buffer tank 720 also includes inlet 710 mechanically coupled to and in fluid communication with a fresh water supply. Outlet 730 of buffer tank 720 is mechanically coupled to and in fluid communication with inlet 740 of pd pump 750. Outlet 760 of pd pump 750 is mechanically coupled to and in fluid communication with inlet 410 of mixing valve 400.

Outlet 510 of centrifuge 500 is mechanically coupled to and in conveyance communication with inlet 770 of receiving bin 780.

Outlet 350 of extractor 330 is mechanically coupled to and in conveyance communication with inlet 770 of receiving bin 780. Inlet 770 of receiving bin 780 is of a 'T' design.

Outlet 160 of pre-screener is mechanically coupled to and in conveyance communication with inlet 210 of receiving bin 220.

Again, referring to FIG. 1, and now describing in detail a preferred method of the invention.

Botanical biomass is introduced into feed hopper 110 at inlet 101 of feed hopper 110. Feed hopper 110 is mechanically coupled to and in conveyance communication with inlet 130 of pre-screener 140 where the botanical biomass is pre-screened to remove undesirables. The pre-screened botanical biomass is discharged at outlet 150 of pre-screener 140 that is mechanically coupled to and in conveyance communication with Screw Conveyor 170. Screw conveyor 170 is mechanically coupled to and in conveyance communication with inlet 180 of Miller 190.

Miller 190 is a component of a system that includes heat exchanger 280 and diverter valve 260, said system taught in U.S. provisional patent application Ser. No. 62/801,672 filed Feb. 6, 2019, the entire contents of which is expressly incorporated herein by reference thereto.

The system that includes Miller 190, heat exchanger 280 and diverter valve 260 each mechanically coupled and in pneumatic communication thus forming a pneumatic circulation loop whereby botanical biomass fed into inlet 180 of Miller 190 will be pneumatically conveyed through Miller 190 where a portion of the botanical biomass surface area will be increased as the botanical biomass is then discharged at outlet 200 of Miller 190. The botanical biomass is then received at inlet 230 of diverter valve 260 where diverter valve 260 is configured to discharge at outlet 240 and then received at inlet 270 of heat exchanger 280. Heat exchanger 280 removes a portion of the heat, sensible and latent, before discharging the chilled botanical biomass at outlet 290 into Screw Conveyor 170 at the point of interface with inlet 180 of Miller 190.

The just described system allows for the botanical biomass to be continuously circulated in a dilute phase within the system with each circulation increasing the SA:V ratio and reducing the temperature of the botanical biomass. After a predetermined period of time, sufficient to adequately increase the SA:V ratio of the bulk botanical biomass to a value greater than 500:1 and remove sufficient heat to reduce the temperature to less than 32° F., diverter valve 260 is configured to discharge at outlet 250 of diverter valve 260. Outlet 250 of diverter valve 260 is mechanically coupled to and in pneumatic communication with feed conveyor 300 and thereby chilled botanical biomass is received into feed conveyor 300. Feed conveyor 300 is mechanically coupled to and in conveyance communication with inlet 310 of extractor 330. Feed conveyor 300 is of a variable speed configuration allowing feed conveyor 300 to regulate the conveyance rate of chilled botanical biomass into inlet 310 of extractor 330.

Extractor 330 disclosed herein is the apparatus taught in U.S. provisional patent application Ser. No. 62/801,671 filed Feb. 6, 2019, the entire contents of which is expressly incorporated herein by reference thereto.

Chilled botanical biomass received at inlet 310 of extractor 330 is introduce onto the interior surface of the rotating cylindrical screen of extractor 330. The rotating speed of the rotating cylindrical screen of extractor 330 is variable. The initial rotating speed of the rotating cylindrical screen of extractor 330 results in a centripetal force equal to less than 1 g during the period where chilled botanical biomass is introduced onto the interior surface of the rotating cylindrical screen of extractor 330 to a predetermined level. Chilled ethanol solvent is introduced onto the interior surface of the rotating cylindrical screen at inlet 320 of extractor 330, inlet 320 of extractor 330 is of a flat spray nozzle design located near the axis of rotation of the rotating cylindrical screen of extractor 330. Chilled ethanol solvent is introduced concurrent with and subsequent to the introduction of the chilled botanical biomass onto the interior surface of the rotating cylindrical screen of extractor 330. The introduction of chilled ethanol solvent will continue for a period of time and in a quantity sufficient to solvate a predetermined amount of the chilled botanical biomass and other soluble constituents of the chilled botanical biomass forming a solution comprising of the chilled ethanol solvent and the solvated constituents of the chilled botanical biomass. The solution is continuously filtered through the rotating cylindrical screen of extractor 330 at a rate determined by the rotating speed of the rotating cylindrical screen of extractor 330.

As previous disclosed the rotating speed of rotating cylindrical screen of extractor 330 is variable. This feature of the rotating cylindrical screen of extractor 330 allows the screen to rotate at a speed resulting in a centripetal force equal to less than 1 g and then at a higher rate of speed resulting in a centripetal force significantly greater than 1 g.

In one example of a preferred method, the rotating cylindrical screen of extractor 330 is first operated at less than 1 g. This will result in a tumbling action of the chilled botanical biomass as the rotating cylindrical screen of extractor 330 rotates. Additionally, the chilled ethanol solvent that is simultaneously introduced onto the interior surface of the rotating cylindrical screen of extractor 330, at inlet 320 of extractor 330, and onto the inner annular formed by the tumbling chilled botanical biomass will tend to remain in contact with the chilled botanical biomass keeping the chilled botanical biomass wet with chilled ethanol solvent. This process will continue for a period of time sufficient to elevate the level of solvated chilled botanical biomass within the chilled ethanol solvent to approximately 50% of the total solubility of the soluble chilled botanical biomass within the chilled ethanol solvent, thus creating a chilled ethanol solution.

Subsequently, the rotating speed of the rotating cylindrical screen of extractor 330 will be increased sufficiently enough to cause the chilled ethanol solution to drain from the surface and subsurface of the chilled botanical biomass. Subsequent to the draining process where the rotating cylindrical screen of extractor 330 is rotating at a speed resulting in a centripetal force significantly greater than 1 g, the rotating cylindrical screen of extractor 330 is slowed to a rotating speed that results in a centripetal force of less than 1 g. This cyclic process where the chilled botanical biomass first wetted with principally clean chilled ethanol solvent and then subsequently dried of the resulting chilled ethanol solution will be repeated a number of times sufficient to solvate principally all of the soluble desirable constituents of the chilled botanical biomass. The chilled ethanol solution drained from the chilled botanical biomass is filtered as it moves from the inner surface of the rotating cylindrical screen of extractor 330 to the outer surface of the rotating cylindrical screen of extractor 330 where it is separated from the rotating cylindrical screen by centripetal force and is received into the integrated chilled ethanol solution receiving tank of extractor 330.

The integrated chilled ethanol solution receiving tank of extractor 330 includes outlet 340 of extractor 330. Outlet 340 of extractor 330 is mechanically coupled to and in fluid communication with inlet 360 of pd pump 370. The chilled ethanol solution discharged at outlet 340 of extractor 330 is received at inlet 360 of pd pump 370. Outlet 380 of pd pump 370 is mechanically coupled to and in fluid communication with intake 390 of mixing valve 400. The chilled ethanol solution is discharged under pressure at outlet 380 of pd pump 370 to be received at inlet 390 of mixing valve 400. Mixing valve 400 features two inlets (inlet 390 and inlet 410) and one outlet (outlet 420). Chilled ethanol solution received at inlet 390 of mixing valve 400 is mixed with water received at inlet 410 of mixing valve 400 at a ratio that results in oversaturation of the ethanol within the chilled ethanol solution causing the undesirable constituents of the chilled ethanol solution to precipitate thus creating a chilled ethanol slurry discharged at outlet 420 of mixing valve 400.

Outlet 420 of mixing valve 400 is mechanically coupled to and in fluid communication with inlet 490 of centrifuge 500. The chilled ethanol slurry is received at inlet 490 of centrifuge 500. In the preferred embodiment of this invention, centrifuge 500 is of a stacked disc, self-cleaning, separator design. This stacked disc, self-cleaning, separator design, is capable of developing a very large centripetal force. The chilled ethanol slurry received at inlet 490 of centrifuge 500 is exposed to a sufficient amount of centripetal force for a sufficient amount of time to settle the precipitate to the inner wall of the rotating element of centrifuge 500. The wall of the rotating element of centrifuge 500 features a valve that is opened hydraulically during operation to allow the precipitate to be discharged at outlet 510 of centrifuge 500. This feature allows for continuous operation of centrifuge 500 without the need to suspend the operation of centrifuge 500 for removal of the precipitate from the inner wall of the rotating element of centrifuge 500. The chilled ethanol solution, now principally free from precipitate, is discharged at outlet 520 of centrifuge 500.

Outlet 520 of centrifuge 500 is mechanically coupled to and in fluid communication with inlet 530 of evaporator 540. The chilled ethanol solution discharged from outlet 520 of centrifuge 500 is received at inlet 530 of evaporator 540. Alternatively, the chilled ethanol solution discharged from outlet 380 of pd pump 370 is received at inlet 530 of evaporator 540. In an embodiment of this invention evaporator 540 is of a falling film, concurrent design. Chilled ethanol solution received at inlet 530 of evaporator 540 is subject to environmental conditions and mechanical interfaces that result in repetitive evaporation and condensing cycles. These cycles effectively separate the ethanol from the chilled ethanol solution. The separated ethanol is discharged from outlet 550 of evaporator 540. The remaining mixture, principally containing water and botanical oil, is discharge at outlet 560 of evaporator 540.

Outlet 560 of evaporator 540 is mechanically coupled to and in fluid communication with inlet 600 of centrifuge 610. The chilled ethanol solution discharged at outlet 560 of evaporator 540 is received at inlet 600 of centrifuge 610. Centrifuge 610 is of a stacked disc, clarifier design and is capable of developing a very large centripetal force and is very efficient at separating the botanical oil from the water where the botanical oil is discharged at outlet 630 of centrifuge 610 and the water is discharged at outlet 620 of centrifuge 610.

Outlet 630 of centrifuge 610 is mechanically coupled to and in fluid communication with inlet 640 of pd pump 650. Clean botanical oil principally free of water, precipitate, and other undesirables is discharged at outlet 630 of centrifuge 610 and received at inlet 640 of pd pump 650. The clean botanical oil is discharged under pressure at outlet 660 of pd pump 650 for further transfer down line.

Outlet 550 of evaporator 540 is mechanically coupled to and in fluid communication with inlet 570 of pd pump 580. Ethanol discharged at outlet 550 of evaporator 540 is received at inlet 570 of pd pump 580. Ethanol discharged under pressure at outlet 590 of pd pump 580 is received at inlet 480 of buffer tank 470.

Outlet 460 of buffer tank 470 is mechanically coupled to and in fluid communication with inlet 450 of pd pump 440. Ethanol is discharged under pressure at outlet 430 of pd pump 440 and received at inlet 320 of extractor 330.

Inlet 320 of extractor 330 is of a flat spray nozzle design.

Outlet 620 of centrifuge 610 is mechanically coupled to and in fluid communication with inlet 670 of pd pump 680. Water discharged at outlet 620 of centrifuge 610 is received at inlet 670 of pd pump 680. Water discharged under pressure at outlet 690 of pd pump 680 is received at inlet 700 of buffer tank 720. Buffer tank 720 features inlet 710. Make up water to compensate for process losses is received at inlet 710 of buffer tank 720.

Outlet 730 of buffer tank 720 is mechanically coupled to and in fluid communication with inlet 740 of pd pump 750. Water discharged at outlet 730 of buffer tank 720 is received at inlet 740 of pd pump 750. Outlet 760 of pd pump 750 is mechanically coupled to and in fluid communication with inlet 410 of mixing valve 400. Water is discharged under pressure at outlet 760 of pd pump 750 in sufficient quantities to meet the demand of mixing valve 400.

Outlet 510 of centrifuge 500 is mechanically coupled to and in conveyance communication with inlet 770 of Receiver Bin 780. Inlet 770 of Receiver Bin is of a "1" design. Precipitate and associated attached liquid discharged at outlet 510 of centrifuge 500 is received at inlet 770 of receiving bin 780.

Outlet 350 of extractor 330 is mechanically coupled to and in conveyance communication with inlet 770 of Receiver Bin 780. Spent botanical biomass and associated attached liquid discharged at outlet 350 of extractor 330 is received at inlet 770 of receiving bin 780.

Outlet 160 of pre-screener 140 is mechanically coupled to and in conveyance communication with inlet 210 of receiving bin 220. Undesirable overflow from the screen of pre-screener 140 is discharged at outlet 160 of pro-screener 140 and received at inlet 210 of receiving bin 220.

Utilizing the new and unique features of the current invention provides for a fully automatic method and system to control the extraction variables associated with solvent type extraction methods, more particularly the variables associated with ethanol extractions of botanical oils, thereby significantly increasing safety, and efficiency while dramatically reducing cost.

Although the present invention and its advantages have been described in detail, it should be understood that various changes, substitutions and alterations may be made herein without departing from the spirit and scope of the invention as defined by the appended claims.

What is claimed is:

1. A method for the extraction of botanical oil from botanical biomass comprising:
   a. pre-screening the botanical biomass,
   b. increasing the surface area of the botanical biomass;
   c. removing heat from the botanical biomass;
   d. introducing the botanical biomass to a suitable solvent;
   e. solvating soluble constituents of the botanical biomass into a suitable solvent thereby forming a first solution;
   f. introducing water to the first solution to precipitate soluble solids thereby forming a slurry;
   g. centrifuging the slurry to remove the precipitated solids thereby forming a second solution;
   h. evaporating the second solution to remove the solvent thereby forming a mixture; and
   i. centrifuging the mixture to isolate the desirable botanical oil.

2. A method for the extraction of botanical oil from botanical biomass comprising:
   a. increasing the surface area of the botanical biomass;
   b. removing heat from the botanical biomass;
   c. introducing the botanical biomass to a suitable solvent;
   d. solvating soluble constituents of the botanical biomass into a suitable solvent thereby forming a first solution; and
   e. evaporating the first solution to remove the solvent thereby forming a mixture.

3. The method for the extraction of botanical oil from botanical biomasses claimed in claim 2 further including pre-screening the botanical biomass of step (a).

4. The method of claim 2 further including the step of introducing water to the first solution to precipitate soluble solids thereby forming a slurry.

5. The method of claim 4 further including the step of centrifuging the slurry to remove the precipitated solids thereby forming a second solution.

6. The method of claim 5 further including the step of centrifuging the mixture to isolate the desirable botanical oil.

* * * * *